(12) United States Patent
Leukel et al.

(10) Patent No.: US 6,713,524 B2
(45) Date of Patent: Mar. 30, 2004

(54) REACTIVE POLYMERS

(75) Inventors: Jörg Leukel, Freiburg (DE); Peter Chabrecek, Riehen (CH); Dieter Lohmann, Münchenstein (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/802,757

(22) Filed: Mar. 9, 2001

(65) Prior Publication Data

US 2003/0194480 A1 Oct. 16, 2003

(30) Foreign Application Priority Data

Mar. 10, 2000 (EP) ............................................. 00105071

(51) Int. Cl.$^7$ .......................... C08F 2/50; C07C 245/00; C07C 247/00; C07C 381/00
(52) U.S. Cl. .............................. 522/49; 522/50; 522/57; 522/62; 522/63; 522/65; 522/167; 522/173; 522/180; 522/8; 522/1; 522/11; 522/12; 534/560; 568/38; 568/41; 568/44; 568/45; 568/301
(58) Field of Search .............................. 522/35, 62, 65, 522/167, 173, 8, 1, 11, 12; 534/560, 561, 564; 568/38, 41

(56) References Cited

U.S. PATENT DOCUMENTS

| | | | | |
|---|---|---|---|---|
| 4,943,648 A | * | 7/1990 | Dicker ........................ | 556/470 |
| 5,002,582 A | | 3/1991 | Guire et al. .................. | 623/66 |
| 5,512,329 A | | 4/1996 | Guire et al. ................. | 427/508 |
| 5,582,955 A | | 12/1996 | Keana et al. ................ | 430/296 |
| 5,685,754 A | * | 11/1997 | Nohr et al. .................... | 442/59 |
| 5,700,921 A | * | 12/1997 | Westling et al. ........... | 536/22.1 |
| 5,741,551 A | | 4/1998 | Guire et al. ............. | 427/407.1 |
| 5,837,746 A | * | 11/1998 | Kohler et al. .................. | 522/8 |
| 6,242,057 B1 | * | 6/2001 | Nohr et al. ................. | 427/513 |
| 6,265,458 B1 | * | 7/2001 | Nohr et al. .................... | 522/6 |
| 6,447,920 B1 | * | 9/2002 | Chabrecek et al. ...... | 428/423.1 |
| 6,468,667 B1 | * | 10/2002 | Chabrecek et al. ......... | 428/532 |
| 6,521,352 B1 | * | 2/2003 | Chabrecek et al. ......... | 428/522 |
| 2002/0122872 A1 | * | 9/2002 | Leukel et al. ................ | 427/2.1 |

FOREIGN PATENT DOCUMENTS

| | | |
|---|---|---|
| EP | 0 700 932 | 1/1995 |
| GB | 0352 149 | 5/1974 |
| WO | WO 98/56372 | 12/1998 |

* cited by examiner

Primary Examiner—Susan Berman
(74) Attorney, Agent, or Firm—Jian S. Zhou; R. Scott Meece; Robert J. Gorman

(57) ABSTRACT

The invention relates to novel reactive polymers of formula

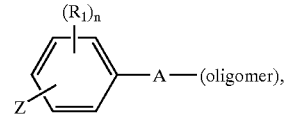

(1)

wherein the variables are as defined in the claims. The polymers of the invention are useful for the modification of material surfaces and are particularly suitable for providing biomedical articles such as contact lenses with a hydrophilic coating.

8 Claims, No Drawings

REACTIVE POLYMERS

The present invention relates to novel highly reactive polymer derivatives, articles such as biomedical articles, especially contact lenses, which are at least partly coated with said polymer derivatives and a process for coating inorganic or organic substrates using the novel polymer derivatives.

A variety of different types of processes for preparing polymeric coatings on a substrate have been disclosed in the prior art. For example, U.S. Pat. No. 5,527,925 describes functionalized photoinitiators and also organic substrates such as contact lenses containing said photoinitiators covalently bound to their surface. In one embodiment of said disclosure, the so modified surface of the contact lens is further coated with a photopolymerizable ethylenically unsaturated monomer which is then polymerized by irradiation thus forming a novel substrate surface. With this method, however, it is not always possible to obtain the desired coating characteristics, for example wettability characteristics which are necessary for the surface of biomedical devices including contact lenses. Most important, the known surface modification process is applicable only to articles having a functionalized surface, that is to say, the surface of the article either inherently contains functional groups or the functional groups have to be introduced previously by a plasma treatment or the like. However, it would be highly desirable to initiate the covalent binding of a hydrophilic layer on an "inert" surface and thereby avoiding a previous plasma treatment or the like.

Surprisingly, now there have been found novel reactive polymer derivatives which are able to react with the surface of articles that is devoid of functional groups. By means of said novel polymers it is possible to obtain articles, particularly biomedical devices such as, for example contact lenses, with an improved wettability, water-retention ability and biocompatibility.

The present invention therefore in one aspect relates to a compound of formula

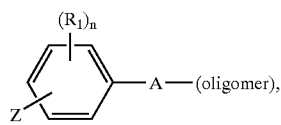

(1)

wherein $R_1$ is an electron-withdrawing substituent and n is an integer from 0 to 2, Z is a group which functions as a precursor for carbene or nitrene formation;

A is a radical of formula

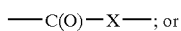  (2a)

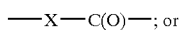  (2b)

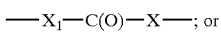  (2c)

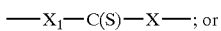  (2d)

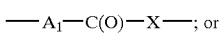  (2e)

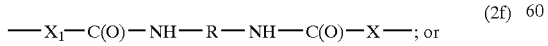  (2f)

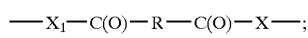  (2g)

X and $X_1$ are each independently of the other a group —O— or —$NR_2$—, wherein $R_2$ is hydrogen or $C_1$–$C_4$-alkyl;

$A_1$ is $C_2$–$C_{30}$-alkyl which may be interrupted by —O—;

R is linear or branched $C_1$–$C_{18}$-alkylene or unsubstituted or $C_1$–$C_4$-alkyl- or $C_1$–$C_4$-alkoxy-substituted $C_6$–$C_{10}$-arylene, $C_7$–$C_{18}$-aralkylene, $C_6$–$C_{10}$-arylene-$C_1$–$C_2$-alkylene-$C_6$–$C_{10}$-arylene, $C_3$–$C_8$-cycloalkylene, $C_3$–$C_8$-cycloalkylene-$C_1$–$C_6$-alkylene, $C_3$–$C_8$-cycloalkylene-$C_1$–$C_2$-alkylene-$C_3$–$C_8$-cycloalkylene or $C_1$–$C_6$-alkylene-$C_3$–$C_8$-cycloalkylene-$C_1$–$C_6$-alkylene; and (oligomer) is (i) the radical of a telomer of formula

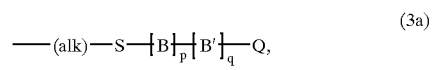

(3a)

wherein (alk) is $C_2$–$C_{12}$-alkylene,

Q is a monovalent group that is suitable to act as a polymerization chain-reaction terminator, p and q are each independently of another an integer from 0 to 750, wherein the total of (p+q) is an integer from 2 to 750, and B and B' are each independently of the other a 1,2-ethylene radical derivable from a copolymerizable vinyl monomer by replacing the vinylic double bond by a single bond, at least one of the radicals B and B' being substituted by a hydrophilic substituent; or (i—i) the radical of a telomer of formula

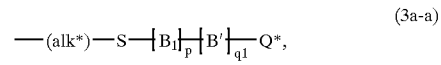

(3a-a)

wherein (alk*) Q*, p1 and q1 each independently have the meaning of (alk), Q, p and q, $B_1$ is a 1,2-ethylene radical derivable from a copolymerizable vinyl monomer by replacing the vinylic double bond by a single bond, which is substituted by a radical —T-(oligomer$^1$), wherein (oligomer$^1$) independently is a radical of formula (3a) above and T is a direct bond or a radical of formula

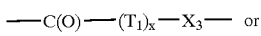  or

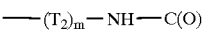

$T_1$ is —O—$C_2$–$C_{12}$-alkylene which is unsubstituted or substituted by hydroxy, or is —O—$C_2$–$C_{12}$-alkylene-NH—C(O)— or —O—$C_2$–$C_{12}$-alkylene-O—C(O)—NH—$R_{13}$—NH—C(O)—, wherein $R_{13}$ independently has the meaning of R above;

$T_2$ is $C_1$–$C_8$-alkylene; phenylene or benzylene;

$X_3$ and $X_4$ are each independently of the other a bivalent group —O— or —$NR_2$', wherein $R_2$' is hydrogen or $C_1$–$C_6$-alkyl;

(alk) is $C_1$–$C_6$-alkylene and (alk*) is $C_2$–$C_{12}$-alkylene, and m and x are each independently of the other the number 0 or 1; and $B_1$' independently has the meaning of $B_1$ or B;

(ii) the radical of an oligomer of the formula

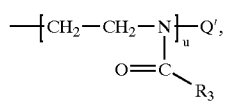
(3b)

wherein $R_3$ is hydrogen or unsubstituted or hydroxy-substituted $C_1$–$C_{12}$-alkyl, u is an integer from 2 to 750 and Q' is a radical of a polymerization initiator; or (iii) the radical of formula

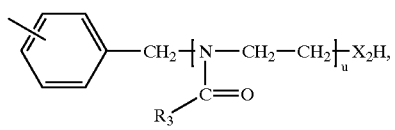
(3b')

wherein $X_2$ independently has the meaning of X above, and $R_3$ and u are as defined above, or (iv) the radical of an oligomer of formula

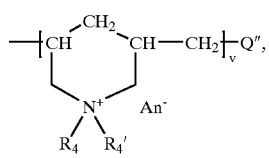
(3c)

wherein $R_4$ and $R_4'$ are each independently $C_1$–$C_4$-alkyl, An⁻ is an anion, v is an integer from 2 to 750, and Q'' is a monovalent group that is suitable to act as a polymerization chain-reaction terminator;

subject to the proviso that A is not a radical of formula (2b) if (oligomer) is a radical of formula (3b) or (3c).

The following preference apply to the variables contained in the definition of the compounds of formula (1):

Z is, for example, a group of formula

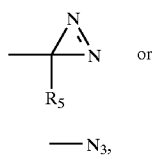
(4a)

—$N_3$, (4b)

wherein $R_5$ is an electron-withdrawing substituent, for example, fluorinated $C_1$–$C_6$-alkyl, for example a radical —$C_2F_5$ or preferably a radical —$CF_3$.

$R_1$ is, for example, hydroxy, $C_1$–$C_4$-alkoxy, nitro, trifluoromethyl or halogen such as, for example, fluorine or chlorine.

The variable n is for example the number 1 or preferably 0.

X and $X_1$ are each independently preferably a group —O— or —NH— and in particular a group —NH— each.

$A_1$ is preferably linear $C_2$–$C_{12}$-alkyl radical witch may be interrupted by —O—, for example a branched or preferably linear $C_2$–$C_{12}$-alkyl radical or in particular a radical —$(CH_2CH_2O)_{1-5}$—$CH_2CH_2$—.

The radicals A of formulae (2a)–(2g) and the radicals of formulae (2a*)–(2e*) are in each case to be understood that the left bond is directed to the phenyl ring or $B_1$ and the right bond is directed to (oligomer) or (oligomer¹), respectively.

R as alkylene in formula (2g) is preferably linear or branched $C_1$–$C_{12}$-alkylene, more preferably $C_1$–$C_6$-alkylene and most preferably $C_1$–$C_4$-alkylene.

R as alkylene in formula (2f) is preferably a linear or branched $C_3$–$C_{14}$alkylene radical, more preferably a linear or branched $C_4$–$C_{12}$alkylene radical and most preferably a linear or branched $C_6$–$C_{10}$-alkylene radical.

When R is arylene, it is, for example, naphthylene or especially phenylene, each of which may be substituted, for example, by $C_1$–$C_4$-alkyl or by $C_1$–$C_4$-alkoxy. Preferably, R as arylene is 1,3- or 1,4-phenylene that is unsubstituted or substituted by $C_1$–$C_4$-alkyl or by $C_1$–$C_4$-alkoxy in the ortho-position to at least one linkage site.

R as aralkylene is preferably naphthylalkylene and most preferably phenylalkylene. The alkylene group in aralkylene contains preferably from 1 to 12, more preferably from 1 to 6 and most preferably from 1 to 4 carbon atoms. Most preferably, the alkylene group in aralkylene is methylene or ethylene.

When R is cycloalkylene, it is preferably $C_5$–$C_6$-cycloalkylene and most preferably cyclohexylene that is unsubstituted or substituted by methyl.

When R is cycloalkylene-alkylene, it is preferably cyclopentylene-$C_1$–$C_4$-alkylene and especially cyclohexylene-$C_1$–$C_4$-alkylene, each unsubstituted or mono- or poly-substituted by $C_1$–$C_4$-alkyl, especially methyl. More preferably, the group cycloalkylene-alkylene is cyclohexylene-ethylene and, most preferably, cyclohexylene-methylene, each unsubstituted or substituted in the cyclohexylene radical by from 1 to 3 methyl groups.

When R is alkylene-cycloalkylene-alkylene, it is preferably $C_1$–$C_4$-alkylene-cyclopentylene-$C_1$–$C_4$-alkylene and especially $C_1$–$C_4$-alkylene-cyclohexylene-$C_1$–$C_4$-alkylene, each unsubstituted or mono- or poly-substituted by $C_1$–$C_4$-alkyl, especially methyl. More preferably, the group alkylene-cycloalkylene-alkylene is ethylene-cyclohexylene-ethylene and, most preferably, is methylene-cyclohexylene-methylene, each unsubstituted or substituted in the cyclohexylene radical by from 1 to 3 methyl groups.

R as $C_3$–$C_8$-cycloalkylene-$C_1$–$C_2$-alkylene-$C_3$–$C_8$-cycloalkylene or $C_6$–$C_{10}$-arylene-$C_1$–$C_2$-alkylene-$C_6$–$C_{10}$-arylene is preferably $C_5$–$C_6$-cycloalkylene-methylene-$C_5$–$C_6$-cycloalkylene or phenylene-methylene-phenylene, each of which may be unsubstituted or substituted in the cycloalkyl or phenyl ring by one or more methyl groups.

The radical R in formula (2f) has a symmetrical or, preferably, an asymmetrical structure.

A preferred group of radicals A comprises those of formula (2f), wherein R is linear or branched $C_6$–$C_{10}$-alkylene; or cyclohexylene-methylene or cyclohexylene-methylene-cyclo-hexylene each unsubstituted or substituted in the cyclohexyl moiety by from 1 to 3 methyl groups.

The bivalent radical R in formula (2f) is derived preferably from a diisocyanate and most preferably from a diisocyanate selected from the group isophorone diisocyanate (IPDI), 4,4'-methylenebis(cyclohexyl isocyanate), 1,6-diisocyanato-2,2,4-trimethyl-n-hexane (TMDI), methylenebis(cyclohexyl-4-isocyanate) and hiexamethylene diisocyanate (HMDI).

In a further embodiment A is preferably a radical of formula (2a), (2b), (2d) or (2e), in particular (2a) or (2b).

One group of suitable compounds of formula (1) are those wherein Z is a group

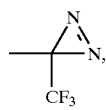

n is 0, and A is a radical of formula (2a).

A further group of suitable compounds of formula (1) are those wherein Z is a group —$N_3$, n is 1 or preferably 0, and A is a radical of formula (2b), (2d) or (2e), in particular (2b).

The hydrophilic polymer (oligomer) has a number average molecular weight $M_n$ of, for example, from 750 to 1000000 Da, preferably of from 1000 to 100000 Da, more preferably from 1500 to 75000 Da, even more preferably from 1500 to 50000 Da, and in particular from 2500 to 50000 Da.

If (oligomer) is a telomer radical (i), (alk) is preferably $C_2$–$C_8$-alkylene, more preferably $C_2$–$C_6$-alkylene, even more preferably $C_2$–$C_4$-alkylene and particularly preferably 1,2-ethylene. The alkylene radical (alk) may be a branched or preferably a linear alkylene radical.

Q may be any chain terminating fragment that is present in the reaction mixture during the preparation of the telomer, for example a hydrogen atom, a solvent radical, an initiator fragment or the radical of the chain transfer agent being used.

The total of (p+q) is preferably an integer from 10 to 750, more preferably from 15 to 700, even more preferably from 20 to 650 and particularly preferably from 40 to 600. In a preferred embodiment of the invention q is 0 and p is an integer from 2 to 750, preferably from 10 to 750, more preferably from 15 to 700, even more preferably from 20 to 650 and particularly preferably from 40 to 600. According to a further embodiment p and q are each independently from 1 to 749 and the total of (p+q) is preferably an integer from 10 to 750, more preferably from 15 to 700, even more preferably from 20 to 650 and particularly preferably from 40 to 600.

Suitable hydrophilic substituents of the radicals B or B' may be non-ionic, anionic, cationic or zwitterionic substituents. Accordingly, the telomer chain of formula (3a) that contains monomer units B and/or B' may be a charged chain containing anionic, cationic and/or zwitterionic groups or may be an uncharged chain. In addition, the telomer chain may comprise a copolymeric mixture of uncharged and charged units. The distribution of the charges within the telomer, if present, may be random or blockwise.

In one preferred embodiment of the invention, the telomer radical of formula (3a) is composed solely of non-ionic monomer units B and/or B'. In another preferred embodiment of the invention, the telomer radical of formula (3a) is composed solely of ionic monomer units B and/or B', for example solely of cationic monomer units or solely of anionic monomer units. Still another preferred embodiment of the invention is directed to telomer radicals of formula (3a) comprising nonionic units B and ionic units B'.

Suitable non-ionic substituents of B or B' include for example $C_1$–$C_6$-alkyl which is substituted by one or more same or different substituents selected from the group consisting of —OH, $C_1$–$C_4$-alkoxy and —$NR_6R_6'$, wherein $R_6$ and $R_6'$ are each independently of another hydrogen or unsubstituted or hydroxy-substituted $C_1$–$C_6$-alkyl or phenyl; phenyl which is substituted by hydroxy, $C_1$–$C_4$-alkoxy or —$NR_6R_6'$, wherein $R_6$ and $R_6'$ are as defined above; a radical —COOY, wherein Y is $C_1$–$C_4$-alkyl, $C_1$–$C_{24}$-alkyl which is substituted, for example, by hydroxy, $C_1$–$C_4$-alkoxy, —O—$Si(CH_3)_3$, —$NR_6R_6'$ wherein $R_6$ and $R_6'$ are as defined above, a radical —O—$(CH_2CH_2O)_{1-24}$—E wherein E is hydrogen or $C_1$–$C_6$-alkyl, or a radical —NH—C(O)—O—G, wherein —O—G is the radical of a saccharide with 1 to 8 sugar units or is a radical —O—$(CH_2CH_2O)_{1-24}$—E, wherein E is as defined above, or Y is $C_5$–$C_8$-cycloalkyl which is unsubstituted or substituted by $C_1$–$C_4$-alkyl or $C_1$–$C_4$-alkoxy, or is unsubstituted or $C_1$–$C_4$-alkyl- or $C_1$–$C_4$-alkoxy-substituted phenyl or $C_7$–$C_{12}$-aralkyl; —$CONY_1Y_2$ wherein $Y_1$ and $Y_2$ are each independently hydrogen, $C_1$–$C_4$-alkyl, $C_1$–$C_{12}$-alkyl, which is substituted, for example by hydroxy, $C_1$–$C_4$-alkoxy or a radical —O—$(CH_2CH_2O)_{1-24}$—E wherein E is as defined above, or $Y_1$ and $Y_2$ together with the adjacent N-atom form a five- or six-membered heterocyclic ring having no additional heteroatom or one additional oxygen or nitrogen atom; a radical —$OY_3$, wherein $Y_3$ is hydrogen; $C_1$–$C_4$-alkyl or $C_1$–$C_{12}$-alkyl which is substituted by —$NR_6R_6'$; or is a radical —C(O)—$C_1$–$C_4$-alkyl; and wherein $R_6$ and $R_6'$ are as defined above; or a five- to seven-membered heterocyclic radical having at least one N-atom and being bound in each case via said nitrogen atom.

Suitable anionic substituents of B or B' include for example $C_1$–$C_6$-alkyl which is substituted by —$SO_3H$, —$OSO_3H$, —$OPO_3H_2$ and —COOH; phenyl which is substituted by one or more same or different substituents selected from the group consisting of —$SO_3H$, —COOH, —OH and —$CH_2$—$SO_3H$; —COOH; a radical —$COOY_4$, wherein $Y_4$ is $C_1$–$C_{24}$-alkyl which is substituted for example by —COOH, —$SO_3H$, —$OSO_3H$, —$OPO_3H_2$ or by a radical —NH—C(O)—O—G' wherein G' is the radical of an anionic carbohydrate; a radical —$CONY_5Y_6$ wherein $Y_5$ is $C_1$–$C_{24}$-alkyl which is substituted by —COOH, —$SO_3H$, —$OSO_3H$, or —$OPO_3H_2$ and $Y_6$ independently has the meaning of $Y_5$ or is hydrogen or $C_1$–$C_{12}$-alkyl; or —$SO_3H$; or a salt thereof, for example a sodium, potassium, ammonium or the like salt thereof.

Suitable cationic substituents of B or B' include $C_1$–$C_{12}$-alkyl which is substituted by a radical —$NR_6R_6'R_6''^+An^-$, wherein $R_6$, $R_6'$ and $R_6''$ are each independently of another hydrogen or unsubstituted or hydroxy-substituted $C_1$–$C_6$-alkyl or phenyl, and $An^-$ is an anion; or a radical —C(O)$OY_7$, wherein $Y_7$ is $C_1$–$C_{24}$-alkyl which is substituted by —$NR_6R_6'R_6''^+An^-$ and is further unsubstituted or substituted for example by hydroxy, wherein $R_6$ $R_6'$, $R_6''$ and $An^-$ are as defined above.

Suitable zwitterionic substituents of B or B' include a radical —$R_7$—Zw, wherein $R_7$ is a direct bond or a functional group, for example a carbonyl, carbonate, amide, ester, dicarboanhydride, dicarboimide, urea or urethane group; and Zw is an aliphatic moiety comprising one anionic and one cationic group each.

The following preferences apply to the hydrophilic substituents of B and B':

(i) non-ionic substituents:
Preferred alkyl substituents of B or B' are $C_1$–$C_4$-alkyl, in particular $C_1$–$C_2$-alkyl, which is substituted by one or more substituents selected from the group consisting of —OH and —$NR_6R_6'$, wherein $R_6$ and $R_6'$ are each independently of another hydrogen or $C_1$–$C_4$-alkyl, preferably hydrogen, methyl or ethyl and particularly preferably hydrogen or methyl, for example —$CH_2$—$NH_2$, —$CH_2$—$N(CH_3)_2$.
Preferred phenyl substituents of B or B' are phenyl which is substituted by —$NH_2$ or $N(C_1$–$C_2$-alkyl$)_2$, for example o-, m- or p-aminophenyl.

In case that the hydrophilic substituent of B or B' is a radical —COOY, Y as alkyl is preferably $C_1$–$C_2$-alkyl; Y as substituted alkyl is preferably $C_1$–$C_{12}$-alkyl, more preferably $C_1$–$C_6$-alkyl, even more preferably $C_1$–$C_4$-alkyl and particularly preferably $C_1$–$C_2$-alkyl, each of which being substituted as mentioned above. In case that the alkyl radical Y is substituted by —$NR_6R_6'$, the above-given meanings and preferences apply for $R_6$ and $R_6'$. Examples of suitable saccharide substituents —O—G of the alkyl radical Y that is substituted by —NH—C(O)—O—G are the radical of a mono- or disaccharide, for example glucose, acetyl glucose, methyl glucose, glucosamine, N-acetyl glucosamine, glucono lactone, mannose, galactose, galactosamine, N-acetyl galactosamine, fructose, maltose, lactose, fucose, saccharose or trehalose, the radical of an anhydrosaccharide such as levoglucosan, the radical of a glucosid such as octylglucosid, the radical of a sugar alcohol such as sorbitol, the radical of a sugar acid derivative such as lactobionic acid amide, or the radical of an oligosaccharide with a maximum of 20 sugar units, for example fragments of a cyclodextrin, a branched cyclodextrin, starch, chitosan, maltotriose or maltohexaose. The radical —O—G preferably denotes the radical of a mono- or disaccharide or the radical of a cyclodextrin fragment with a maximum of 8 sugar units. Particular preferred saccharide radicals —O—G are the radical of trehalose or the radical of a cyclodextrin fragment. In case that the alkyl radical Y is substituted by a radical —O—$(CH_2CH_2O)_{1-24}$—E or —NH—C(O)—O—G wherein —O—G is —O—$(CH_2CH_2O)_{1-24}$—E, the number of $(CH_2CH_2O)$ units is preferably from 1 to 12 in each case and more preferably from 2 to 8. E is preferably hydrogen or $C_1$–$C_2$-alkyl. Y as $C_5$–$C_8$-cycloalkyl is for example cyclopentyl or preferably cyclohexyl, each of which being unsubstituted or substituted for example by 1 to 3 $C_1$–$C_2$-alkyl groups. Y as $C_7$–$C_{12}$-aralkyl is for example benzyl.

Preferred nonionic radicals —COOY are those wherein Y is $C_1$–$C_2$-alkyl; or $C_2$–$C_6$-alkyl which is substituted by one or two substituents selected from the group consisting of hydroxy; $C_1$–$C_2$-alkoxy; —O—$Si(CH_3)_3$; and —$NR_{23}R_{23}'$ wherein $R_{23}$ and $R_{23}'$ are each independently of another hydrogen or $C_1$–$C_4$-alkyl; or Y is a radical —$CH_2CH_2$—O—$(CH_2CH_2O)_{1-12}$—E wherein E is hydrogen or $C_1$–$C_2$-alkyl; or is a radical —$C_2$–$C_4$-alkylene-NH—C(O)—O—G, wherein —O—G is the radical of a saccharide.

More preferred non-ionic radicals —COOY are those wherein Y is $C_1$–$C_2$-alkyl; or $C_2$–$C_4$-alkyl which is substituted by one or two substituents selected from the group consisting of —OH and —$NR_6R_6'$ wherein $R_6$ and $R_6'$ are each independently of another hydrogen or $C_1$–$C_2$-alkyl; or a radical —$CH_2CH_2$—O—$(CH_2CH_2O)_{1-12}$—E wherein E is hydrogen or $C_1$–$C_2$-alkyl; or is a radical —$C_2$–$C_4$-alkylene-NH—C(O)—O—G wherein —O—G is the radical of a saccharide.

Particularly preferred radicals —COOY comprise those wherein Y is $C_1$–$C_2$-alkyl, particularly methyl; or $C_2$–$C_3$-alkyl, which is unsubstituted or substituted by hydroxy or N,N-di-$C_1$–$C_2$-alkylamino, or is a radical -$C_2$–$C_3$-alkylene—NH—C(O)—O—G wherein —O—G is the radical of trehalose or the radical of a cyclodextrin fragment with a maximum of 8 sugar units.

Preferred non-ionic substituents —C(O)—$NY_1Y_2$ of B or B' are those wherein $Y_1$ and $Y_2$ are each independently of the other hydrogen, $C_1$–$C_2$-alkyl or $C_1$–$C_6$-alkyl which is substituted by hydroxy; or $Y_1$ and $Y_2$ together with the adjacent N-atom form a heterocyclic 6-membered ring having no further heteroatom or having one further N- or O-atom. Even more preferred meanings of $Y_1$ and $Y_2$, independently of each other, are hydrogen, $C_1$–$C_2$-alkyl or $C_1$–$C_4$-alkyl which is unsubstituted or substituted by hydroxy; or $Y_1$ and $Y_2$ together with the adjacent N-atom form a N—$C_1$–$C_2$-alkylpiperazino or morpholino ring. Particularly preferred non-ionic radicals —C(O)—$NY_1Y_2$ are those wherein $Y_1$ and $Y_2$ are each independently of the other hydrogen, methyl or 2-hydroxyethyl; or $Y_1$ and $Y_2$ together with the adjacent N-atom form a morpholino ring.

Preferred non-ionic substituents —$OY_3$ of B or B' are those wherein $Y_3$ is hydrogen, $C_1$–$C_2$-alkyl, $C_1$–$C_4$-alkyl which is substituted by —$NH_2$ or —$N(C_1$–$C_2$-alkyl$)_2$, or is a group —$C(O)C_1$–$C_2$-alkyl. $Y_3$ is particularly preferred hydrogen or acetyl.

Preferred non-ionic heterocyclic substituents of B or B' are a 5- or 6-membered heteroaromatic or heteroaliphatic radical having one N-atom and in addition no further heteroatom or an additional N- or O-heteroatom, or is a 5 to 7-membered lactame. Examples of such heterocyclic radicals are N-pyrrolidonyl, 2- or 4-pyridinyl, 2-methyl pyridin-5-yl, 2-, 3-oder 4-hydroxypyridinyl, N-ε-caprolactamyl, N-imidazolyl, 2-methylimidazol-1-yl, N-morpholinyl or 4-N-methylpiperazin-1-yl, particularly N-morpholinyl or N-pyrrolidonyl.

A group of preferred non-ionic substituents of B or B' comprises $C_1$–$C_2$-alkyl, which is unsubstituted or substituted by —OH or —$NR_6R_6'$, wherein $R_6$ and $R_5'$ are each independently of the other hydrogen or $C_1$–$C_2$-alkyl; a radical —COOY wherein Y is $C_1$–$C_2$-alkyl; $C_2$–$C_4$-alkyl which is substituted by —OH, —$NR_6R_6'$ wherein $R_6$ and $R_6'$ are each independently of another hydrogen or $C_1$–$C_2$-alkyl, or Y is a radical —$C_2$–$C_4$-alkylene-NH—C(O)—O—G wherein —O—G is the radical of a saccharide; a radical —C(O)—$NY_1Y_2$, wherein $Y_1$ and $Y_2$ are each independently of the other hydrogen, $C_1$–$C_2$-alkyl or $C_1$–$C_6$-alkyl which is unsubstituted or substituted by hydroxy, or $Y_1$ and $Y_2$ together with the adjacent N-atom form a heterocyclic 6-membered ring having no further heteroatom or having one further N—or O-atom; a radical —$OY_3$, wherein $Y_3$ is hydrogen, $C_1$–$C_2$-alkyl, $C_1$–$C_4$-alkyl which is substituted by —$NH_2$ or —$N(C_1$–$C_2$-alkyl$)_2$, or is a group —$C(O)C_1$–$C_2$-alkyl; or a 5–or 6-membered heteroaromatic or heteroaliphatic radical having one N-atom and in addition no further heteroatom or an additional N-, O- or S-heteroatom, or a 5 to 7-membered lactame.

A group of more preferred non-ionic substituents of B or B' comprises a radical —COOY, wherein Y is $C_1$–$C_2$-alkyl, $C_2$–$C_3$-alkyl, which is substituted by hydroxy, amino or N,N-di-$C_1$–$C_2$-alkylamino, or is a radical —$C_2$–$C_4$-alkylene-NH—C(O)—O—G wherein —O—G is the radical of trehalose or a cyclodextrin fragment with a maximum of 8 sugar units; a radical —CO—$NY_1Y_2$, wherein $Y_1$ and $Y_2$ are each independently of the other hydrogen, $C_1$–$C_2$-alkyl or $C_1$–$C_4$-alkyl which is substituted by hydroxy, or $Y_1$ and $Y_2$ together with the adjacent N-atom form a N—$C_1$–$C_2$-alkylpiperazino or morpholino ring; or a heterocyclic radical selected from the group consisting of N-pyrrolidonyl, 2- or 4-pyridinyl, 2-methylpyridin-5-yl, 2-, 3-oder 4-hydroxypyridinyl, N-ε-caprolactamyl, N-imidazolyl, 2-methylimidazol-1-yl, N-morpholinyl and 4-N-methylpiperazin-1-yl.

A particularly preferred group of non-ionic substituents of B or B' comprises the radicals —COO—$C_1$–$C_2$-alkyl, —COO—$(CH_2)_{2-4}$—OH, —$CONH_2$, —$CON(CH_3)_2$, —CONH—$(CH_2)_2$—OH,

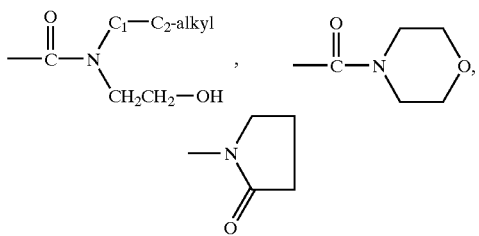

and —COO(CH$_2$)$_{2-4}$—NHC(O)—O—G
wherein —O—G is the radical of trehalose or a cyclodextrin fragment with a maximum of 8 sugar units.

(ii) anionic substituents:

Preferred anionic substituents of B or B' are C$_1$–C$_4$-alkyl, in particular C$_1$–C$_2$-alkyl, which is substituted by one or more substituents selected from the group consisting of —SO$_3$H and —OPO$_3$H$_2$, for example —CH$_2$—SO$_3$H; phenyl which is substituted by —SO$_3$H or sulfomethyl, for example o- , m- or p-sulfophenyl or o- , m- or p-sulfomethylphenyl; —COOH; a radical —COOY$_4$, wherein Y$_4$ is C$_2$–C$_6$-alkyl which is substituted by —COOH, —SO$_3$H, —OSO$_3$H, —OPO$_3$H$_2$, or by a radical —NH—C(O)—O—G' wherein G' is the radical of lactobionic acid, hyaluronic acid, sialic acid or of a sialic acid terminated carbohydrate, for example sialidated galactose or lactobionic acid; in particular C$_2$–C$_4$-alkyl which is substituted by —SO$_3$H or —OSO$_3$H; a radical —CONY$_5$Y$_6$ wherein Y$_5$ is C$_1$–C$_6$-alkyl substituted by sulfo, in particular C$_2$–C$_4$-alkyl substituted by sulfo, and Y$_6$ is hydrogen, for example the radical —C(O)—NH—C(CH$_3$)$_2$—CH$_2$—SO$_3$H; or —SO$_3$H; or a suitable salt thereof, for example the sodium or potassium salt or a biocompatible amine salt such as the triethanolamine salt. Particular preferred anionic substituents of B or B' are —COOH, —SO$_3$H, o- , m- or p-sulfophenyl, o- , m- or p-sulfomethylphenyl or a radical —CONY$_5$Y$_6$ wherein Y$_5$ is C$_2$–C$_4$-alkyl substituted by sulfo, and Y$_6$ is hydrogen.

(iii) cationic substituents:

Preferred cationic substituents of B or B' are C$_1$–C$_4$-alkyl, in particular C$_1$–C$_2$-alkyl, which is in each case substituted by —NR$_6$R$_6$'R$_6$''$^+$An$^-$; or a radical —C(O)OY$_7$ wherein Y$_7$ is C$_2$–C$_6$-alkyl, in particular C$_2$–C$_4$-alkyl, which is in each case substituted by —NR$_6$R$_6$'R$_6$''$^+$An$^-$ and is further unsubstituted or substituted by hydroxy. R$_6$, R$_6$' and R$_6$'' are each independently of another preferably hydrogen or C$_1$–C$_4$-alkyl, more preferably methyl or ethyl and particularly preferably methyl. Examples of suitable anions An$^-$ are Hal$^-$, wherein Hal is halogen, for example Br$^-$, F$^-$, J$^-$ or particularly Cl$^-$, furthermore HCO$_3^-$, CO$_3^{2-}$, H$_2$PO$_4^-$, HPO$_4^{2-}$, PO$_4^{3-}$, HSO$_4^-$, SO$_4^{2-}$ or the radical of an organic acid such as OCOCH$_3^-$ and the like. A particularly preferred cationic substituent of B or B' is a radical —C(O)OY$_7$ wherein Y$_7$ is C$_2$–C$_4$-alkyl, which is substituted by —N(C$_1$–C$_2$-alkyl)$_3^+$An$^-$ and is further substituted by hydroxy, and An$^-$ is an anion, for example the radical —C(O)O—CH$_2$—CH(OH)—CH$_2$—N(CH$_3$)$_3^+$An$^-$.

(iv) zwitterionic substituents —R$_7$—Zw:

R$_7$ is a preferably a carbonyl, ester or amide functional group and more preferably an ester group —C(O)—O—.

Suitable anionic groups of the moiety Zw are for example —COO$^-$, —SO$_3^-$, —OSO$_3^-$, —OPO$_3$H$^-$ or bivalent —O—PO$_2^-$— or —O—PO$_2^-$—O—, preferably a group —COO$^-$ or —SO$_3^-$ or a bivalent group —O—PO$_2^-$—, and in particular a group —SO$_3^-$.

Suitable cationic groups of the moiety Zw are for example a group —NR$_6$R$_6$'R$_6$''$^+$ or a bivalent group —NR$_6$R$_6$'$^+$—, wherein R$_6$, R$_6$' and R$_6$'' are as defined above, and are each independently of the other, preferably hydrogen or C$_1$–C$_6$-alkyl, preferably hydrogen or C$_1$–C$_4$-alkyl and most preferably each methyl or ethyl.

The moiety Zw is for example C$_2$–C$_{30}$-alkyl, preferably C$_2$–C$_{12}$-alkyl, and more preferably C$_3$–C$_8$-alkyl, which is in each case uninterrupted or interrupted by —O—, and substituted or interrupted by one of the above-mentioned anionic and cationic groups each, and, in addition, is further unsubstituted or substituted by a radical —OY$_8$, wherein Y$_8$ is hydrogen or the acyl radical of a carboxylic acid.

Y$_8$ is preferably hydrogen or the acyl radical of a higher fatty acid.

A further embodiment relates to zwitterionic moieties wherein R$_7$ is a group —C(O)NH— and Zw is a radical of formula $$—(CHR_8—C(O)—NH)_t—CHR_8—COOH \quad (5),$$

wherein R$_8$ is hydrogen or C$_1$–C$_4$-alkyl which is unsubstituted or substituted by hydroxy, carboxy, carbamoyl, amino, phenyl, o- ,m- or p-hydroxyphenyl, imidazolyl, indolyl or a radical —NH—C(=NH)—NH$_2$ and t is an integer from 2 to 250, or Zw is the radical of an oligopeptide based on proline or hydroxyproline.

Zw is preferably C$_2$–C$_{12}$-alkyl and even more preferably C$_3$–C$_8$-alkyl which is substituted or interrupted by one of the above-mentioned anionic and cationic groups each, and in addition may be further substituted by a radical —OY$_8$.

A preferred group of zwitter-ionic substituents —R$_7$—Zw corresponds to the formula

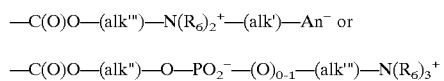

wherein R$_6$ is hydrogen or C$_1$–C$_6$-alkyl; An$^-$ is an anionic group —COO$^-$, —SO$_3^-$, —OSO$_3^-$ or —OPO$_3$H$^-$, preferably —COO$^-$ or —SO$_3^-$ and most preferably —SO$_3^-$, alk' is C$_1$–C$_{12}$-alkylene, (alk'') is C$_2$–C$_{24}$-alkylene which is unsubstituted or substituted by a radical —OY$_8$, Y$_8$ is hydrogen or the acyl radical of a carboxylic acid, and (alk''') is C$_2$–C$_8$-alkylene.

(alk') is preferably C$_2$–C$_8$-alkylene, more preferably C$_2$–C$_6$-alkylene and most preferably C$_2$–C$_4$-alkylene. (alk'') is preferably C$_2$–C$_{12}$-alkylene, more preferably C$_2$–C$_6$-alkylene and particularly preferably C$_2$–C$_3$-alkylene which is in each case unsubstituted or substituted by hydroxy or by a radical —OY$_8$. (alk''') is preferably C$_2$–C$_4$-alkylene and more preferably C$_2$–C$_3$-alkylene. R$_9$ is hydrogen or C$_1$–C$_4$-alkyl, more preferably methyl or ethyl and particularly preferably methyl. A preferred zwitterionic substituent of B or B' is of formula

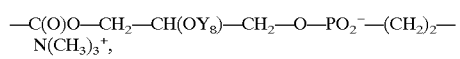

wherein Y$_8$ is hydrogen or the acyl radical of a higher fatty acid.

B denotes for example a radical of formula

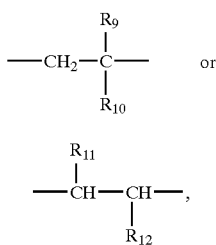

wherein $R_9$ is hydrogen or $C_1$–$C_4$-alkyl, preferably hydrogen or methyl; $R_{10}$ is a hydrophilic substituent, wherein the above given meanings and preferences apply; $R_{11}$ is $C_1$–$C_4$-alkyl, phenyl or a radical —C(O)O$Y_9$, wherein $Y_9$ is hydrogen or unsubstituted or hydroxy-substituted $C_1$–$C_4$-alkyl; and $R_{12}$ is a radical —C(O)$Y_9'$ or —CH$_2$—C(O)O$Y_9'$ wherein $Y_9'$ independently has the meaning of $Y_9$.

$R_{11}$ is preferably $C_1$–$C_2$-alkyl, phenyl or a group —C(O)O$Y_9$. $R_{12}$ is preferably a group —C(O)O$Y_9'$ or —CH$_2$—C(O)O$Y_9'$ wherein $Y_9$ and $Y_9'$ are each independently of the other hydrogen, $C_1$–$C_2$-alkyl or hydroxy-$C_1$–$C_2$-alkyl. Particularly preferred —CHR$_{11}$–CHR$_{12}$— units according to the invention are those wherein $R_{11}$ is methyl or a group —C(O)O$Y_9$ and $R_{12}$ is a group —C(O)O$Y_9'$ or —CH$_2$—C(O)O$Y_9'$ wherein $Y_9$ and $Y_9'$ are each hydrogen, $C_1$–$C_2$-alkyl or hydroxy-$C_1$–$C_2$-alkyl.

B' independently may have one of the meanings given above for B.

If (oligomer) is a radical of formula (3a), the radical —(alk)—S—[B]$_p$—[B']$_q$—Q preferably denotes a radical of formula

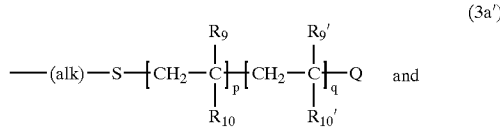

even more preferably of the formula

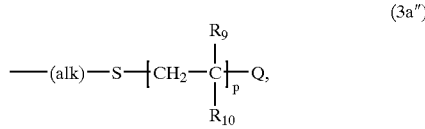

wherein for $R_9$, $R_{10}$, Q, p and q the above-given meanings and preferences apply, for $R_9'$ independently the meanings and preferences given before for $R_9$ apply, and for $R_{10}'$ independently the meanings and preferences given before for $R_{10}$ apply.

One embodiment of radicals (oligomer) concerns those radicals of formula (3a') or (3a"), wherein $R_9$ and $R_9'$ are each independently hydrogen or methyl and $R_{10}$ and $R_{10}'$ are each independently one of the above-mentioned low molecular weight hydrophilic radicals, for example a radical having a weight average molecular weight of <200; Suitable low-molecular weight radicals in this context are, for example, a non-ionic radical selected from the group of $C_1$–$C_2$-alkyl, which is unsubstituted or substituted by —OH or —NR$_6$R$_6'$, wherein $R_6$ and $R_6'$ are each independently of the other hydrogen or $C_1$–$C_2$-alkyl; a radical —COOY wherein Y is $C_1$–$C_2$-alkyl; $C_2$–$C_4$-alkyl which is substituted by —OH, —NR$_6$R$_6'$ wherein $R_6$ and $R_6'$ are each independently of another hydrogen or $C_1$–$C_2$-alkyl; a radical —C(O)—NY$_1$Y$_2$, wherein $Y_1$ and $Y_2$ are each independently of the other hydrogen, $C_1$–$C_2$-alkyl or $C_1$–$C_6$-alkyl which is unsubstituted or substituted by hydroxy, or $Y_1$ and $Y_2$ together with the adjacent N-atom form a heterocyclic 6-membered ring having no further heteroatom or having one further N- or O-atom; a radical —OY$_3$, wherein $Y_3$ is hydrogen, $C_1$–$C_2$-alkyl, $C_1$–$C_4$-alkyl which is substituted by —NH$_2$ or —N(C$_1$–$C_2$-alkyl)$_2$, or is a group —C(O)C$_1$–$C_2$-alkyl; and a 5- or 6-membered heteroaromatic or heteroaliphatic radical having one N-atom and in addition no further heteroatom or an additional N-, O- or S-heteroatom, or a 5 to 7-membered lactame; an anionic radical selected from —COOH, —SO$_3$H, o-, m- or p-sulfophenyl, o-, m- or p-sulfomethylphenyl or a radical —CONY$_5$Y$_6$ wherein $Y_5$ is $C_2$–$C_4$-alkyl substituted by sulfo, and $Y_6$ is hydrogen; a cationic radical selected from $C_1$–$C_4$-alkyl, in particular $C_1$–$C_2$-alkyl, which is in each case substituted by —NR$_6$R$_6'$R$_6''^+$An$^-$; or a radical —C(O)O$Y_7$ wherein $Y_7$ is $C_2$–$C_6$-alkyl, in particular $C_2$–$C_4$-alkyl, which is in each case substituted by —NR$_6$R$_6'$R$_6''^+$An$^-$ and is further unsubstituted or substituted by hydroxy; or a zwitterionic radical selected from

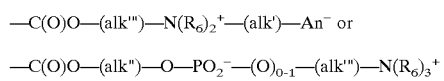

wherein $R_6$ is hydrogen or $C_1$–$C_2$-alkyl; An$^-$ is an anionic group —COO$^-$, —SO$_3^-$, —OSO$_3^-$ or —OPO$_3$H$^-$, alk' is $C_2$–$C_4$-alkylene, (alk") is $C_2$–$C_3$-alkylene which is unsubstituted or substituted by hydroxy, and (alk''') is $C_2$–$C_4$-alkylene.

A further embodiment of radicals (oligomer) concerns those radicals of formula (3a') or (3a"), wherein $R_9$ and $R_9'$ are each independently hydrogen or methyl, at least one $R_{10}$ is a radical comprising a hydrophilic side chain having a weight average molecular weight of ≧200; and $R_{10}'$ independently has the meaning of $R_{10}$ or is a low molecular weight radical as mentioned above. $R_{10}$ or $R_{10}'$ as a radical comprising a hydrophilic side chain in this context are, for example a non-ionic substituent selected from the group consisting of a radical —COOY, wherein Y is a radical —CH$_2$CH$_2$—O—(CH$_2$CH$_2$O)$_y$—E, E is hydrogen or $C_1$–$C_6$-alkyl and y is an integer from 3 to 24, or Y is a radical —C$_2$–C$_6$-alkyl-NH—C(O)—O—G wherein —O—G is the radical of a saccharide or is a radical —O—(CH$_2$CH$_2$O)$_y$—E wherein E and y are each as defined above; and a radical —CONY$_1$Y$_2$, wherein $Y_1$ is hydrogen or unsubstituted or, for example, hydroxy-substituted $C_1$–$C_{12}$-alkyl, and $Y_2$ is $C_1$–$C_{12}$-alkyl which is substituted by a radical —O—(CH$_2$CH$_2$O)$_y$—E and wherein E and y are as defined above; and a zwitter-ionic substituent selected from a group of formula

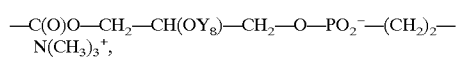

wherein $Y_8$ is the acyl radical of a higher fatty acid, and a group of formula

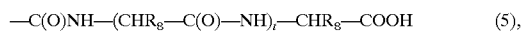

wherein $R_8$ is hydrogen or $C_1$–$C_4$-alkyl which is unsubstituted or substituted by hydroxy, carboxy, carbamoyl, amino, phenyl, o-, m- or p-hydroxyphenyl, imidazolyl, indolyl or a radical —NH—C(=NH)—NH$_2$ and t is an integer from 2 to 250.

If (oligomer) is a radical (i—i) of formula (3a—a), the following preferences apply for the variables contained therein:

For (alk*), Q*, p1 and q1 independently the preferences given above for (alk), Q, p and q apply. (oligomer$^1$) is a radical of formula (3a) wherein the above-given meanings and preferences apply.

$X_3$ is preferably a bivalent group —O— or —NH—, in particular —NH—. $X_4$ is preferably —O— or —NH—.

For $R_{13}$ independently the meanings and preferences given above for R in formula (2f) apply.

Preferred meanings of $T_1$ are unsubstituted or hydroxy-substituted —O—$C_2$-$C_8$-alkylene or a radical —O—$C_2$-$C_6$-alkylene-NH—C(O)— and particularly —O—(CH$_2$)$_{2-4}$—, —O—CH$_2$—CH(OH)—CH$_2$— or a radical —O—(CH$_2$)$_{2-4}$—NH—C(O)—. A particularly preferred meaning of $T_1$ is the radical —O—(CH$_2$)$_2$—NH—C(O)—. $T_2$ is preferably $C_1$-$C_6$-alkylene, phenylene or benzylene, more preferably $C_1$-$C_4$-alkylene and even more preferably $C_1$-$C_2$-alkylene. x is an integer of 0 or preferably 1. m is preferably an integer of 1.

T is preferably a radical of formula (2b*) or in particular (2a*).

A preferred group of radicals $B_1$ comprises radicals of the formula

(6a')

wherein $R_9$ is hydrogen or $C_1$-$C_4$-alkyl, preferably hydrogen or methyl, and $R_{10}$ is a radical —T—(oligomer$^1$) wherein T is a radical of the formula (2a*) or (2b*) and (oligomer$^1$) is a radical of formula (3a), where the above given meanings and preferences apply. An even more preferred group of radicals $B_1$ comprises radicals of the above formula (6a'), wherein $R_9$ is hydrogen or methyl, and $R_{10}$* is a radical —T—(oligomer$^1$), wherein T is a radical of the formula (2a*) and (oligomer$^1$) is a radical of formula (3a).

A preferred radical $B_1$ is, for example a radical of formula

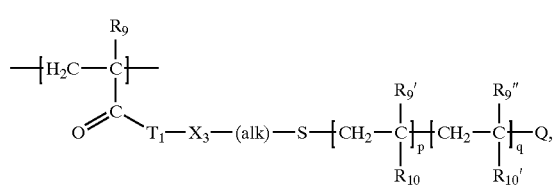

(6a'')

where $R_9$, $R_9$' and $R_9$" are each independently hydrogen or methyl, $T_1$ is —O—(CH$_2$)$_{2-4}$—, —O—CH$_2$—CH(OH)—CH$_2$— or a radical —O—(CH$_2$)$_{2-4}$—NH—C(O)—, $X_3$ is —O— or —NH—, (alk) is $C_2$-$C_4$-alkylene, Q is a monovalent group that is suitable to act as a polymerization chain-reaction terminator, and for $R_{10}$, $R_{10}$', p and q each independently the above given meanings and preferences apply.

A particularly preferred radical $B_1$ is of the formula

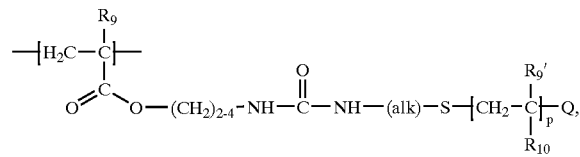

(6a''')

wherein $R_9$ and $R_9$' are each independently hydrogen or methyl, and for $R_{10}$, Q, (alk) and p the above-given meanings and preferences apply. A particularly preferred group of radicals of the above formula (6a''') are those wherein $R_9$ and $R_9$' are each independently hydrogen or methyl, (alk) is $C_2$-$C_4$-alkylene, p is an integer of 10 to 750, Q is as defined before, and for $R_{10}$ the above given meanings and preferences apply; in particular $R_{10}$ of this embodiment is a radical

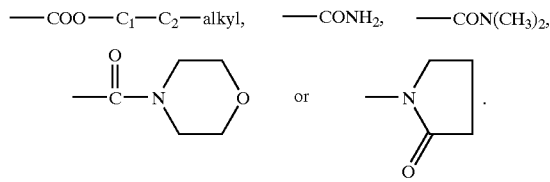

The radical $B_1$' is preferably independently a radical B wherein the above-given meanings and preferences apply. The variable q1 is most preferably 0 and for p1 independently the above-given meanings and preferences for p apply.

If (oligomer) is a radical (ii) of formula (3b), Q' in formula (3b) is for example $C_1$-$C_{12}$-alkyl, phenyl or benzyl, preferably $C_1$-$C_2$-alkyl or benzyl and in particular methyl. $R_3$ is preferably unsubstituted or hydroxy-substituted $C_1$-$C_4$-alkyl and in particular methyl. u is preferably an integer from 2 to 500, more preferably from 5 to 500, even more preferably from 5 to 250 and particularly preferably from 10 to 100.

If (oligomer) is a radical (iii) of formula (3b'), the above given meanings and preferences apply for the variables $R_3$ and u contained therein. The radical $X_2$H in formula (3b') is preferably hydroxy or amino.

If (oligomer) denotes a radical (iv) of formula (3c), $R_4$ and $R_4$' are each preferably ethyl or in particular methyl; v is preferably an integer from 2 to 500, more preferably from 5 to 500, even more preferably from 5 to 250 and particularly preferably from 10 to 100; Q" is for example hydrogen; and An is as defined before.

Formulae (3a), (3a—a), (3a') and (6a") are to be understood as a statistic description of the respective oligomeric radicals, that is to say, the orientation of the monomers and the sequence of the monomers (in case of copolymers) are not fixed in any way by said formulae. The arrangement of B and B' in formulae (3a), (3a—a) or (3a') thus in each case may be random or blockwise.

The compounds of formula (1) may be prepared, for example, by reacting a compound of formula

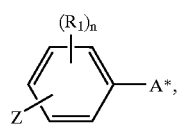

(7)

wherein A* is amino, N—$C_1$–$C_4$-alkylamino, hydroxy, isocyanato, isothiocyanato, carboxy, or a carboxy derivative, for example an acid halide, ester or anhydride, and $R_1$, Z and n are as defined above, with a compound of formula

(8), wherein (oligomer) is as defined above, and A** independently has the meaning of A* with the proviso that A** is coreactive to A*:

For example, the reactions of a compound of formula (7) having a carboxy, carboxylic acid halide group, ester, acid anhydride, isocyanato group or isothiocyanato group with an amino or hydroxy compound of formula (8), or vice versa, are well-known in the art and may be carried out as described in textbooks of organic chemistry. For example, the reaction of an isocyanato or isothiocyanato derivative of formula (7) with an amino- or hydroxy-compound of formula (8) may be carried out in an inert organic solvent such as an optionally halogenated hydrocarbon, for example petroleum ether, methylcyclohexane, toluene, chloroform, methylene chloride and the like, or an ether, for example diethyl ether, tetrahydrofurane, dioxane, or a more polar solvent such as DMSO, DMA, N-methyl-pyrrolidone or even a lower alcohol, at a temperature of from 0 to 100° C., preferably from 0 to 50° C. and particularly preferably at room temperature, optionally in the presence of a catalyst, for example a tertiary amine such as triethylamine or tri-n-butylamine, 1,4-diazabicyclooctane, or a tin compound such as dibutyltin dilaurate or tin dioctanoate. It is advantageous to carry out the above reactions under an inert atmosphere, for example under an nitrogen or argon atmosphere.

In case of a compound of formula (7) or (8) carrying a carboxy anhydride group, the reaction of the carboxy anhydride with a compound of formula (8) or (7) carrying an amino or hydroxy group may be carried out as described in organic textbooks, for example in an aprotic solvent, for example one of the above-mentioned aprotic solvents, at a temperature from room temperature to about 100° C.

In case of a compound of formula (7) or (8) carrying a carboxy group, the reaction of the carboxy group with a compound of formula (8) or (7) carrying an amino or hydroxy group may be carried out under the conditions that are customary for ester or amide formation, for example in an aprotic medium at a temperature from about room temperature to about 100° C. It is further preferred to carry out the esterification or amidation reaction in the presence of an activating agent, for example N-ethyl-N'-(3-dimethylaminopropyl)carbodiimide (EDC), N-hydroxy succinimide (NHS) or N,N'-dicyclohexyl carbodiimide (DCC).

The compounds of formula (1) may be isolated in a manner known per se and are advantageously purified before use, for example by precipitation with a suitable solvent, filtration and washing, extraction in a suitable solvent, dialysis, reverse osmoses (RO) or ultrafiltration, reverse osmoses and ultrafiltration being especially preferred.

The preferred purification processes for the copolymers of the invention, reverse osmoses and ultrafiltration, can be carried out in a manner known per se. It is possible for the ultrafiltration and reverse osmoses to be carried out repeatedly, for example from two to ten times. Alternatively, the ultrafiltration and reverse osmoses can be carried out continuously until the selected degree of purity is attained. The selected degree of purity can in principle be as high as desired.

The compounds of formula (7) are known and partly commercially available or may be prepared according to known processes. The compounds of formula (8) are likewise known, for example from WO 99/57581, or may be obtained according to processes known in the art.

A further object of the invention concerns a composite material comprising
(a) an inorganic or organic bulk material; and
(b) a hydrophilic surface coating obtainable by applying one or more different compounds of the formula (1) wherein for the variables contained therein the above given meanings and preferences apply, to the bulk material surface.

Examples of inorganic or organic bulk materials according to (a) are quartz, ceramics, glasses, silicate minerals, silica gels, metals, metal oxides, carbon materials such as graphite or glassy carbon, natural or synthetic organic polymers, or laminates, composites or blends of said materials, in particular natural or synthetic organic polymers which are known in large number. Some examples of polymers are polyaddition and polycondensation polymers (polyurethanes, epoxy resins, polyethers, polyesters, polyamides and polyimides); vinyl polymers (polyacrylates, polymethacrylates, polystyrene, polyethylene and halogenated derivatives thereof, polyvinyl acetate and polyacrylonitrile); or elastomers (silicones, polybutadiene and polyisoprene).

A preferred group of materials to be coated are those being conventionally used for the manufacture of biomedical devices, e.g. contact lenses, in particular contact lenses, which are not hydrophilic per se. Such materials are known to the skilled artisan and may comprise for example polysiloxanes, perfluoropolyethers, fluorinated poly(meth) acrylates or equivalent fluorinated polymers derived e.g. from other polymerizable carboxylic acids, polyalkyl (meth) acrylates or equivalent alkylester polymers derived from other polymerizable carboxylic acids, polyolefines, or fluorinated polyolefines, such as polyvinylidene fluoride, fluorinated ethylene propylene, or tetrafluoroethylene, preferably in combination with specific dioxols, such as perfluoro-2,2-dimethyl-1,3-dioxol. Examples of suitable bulk materials are e.g. Lotrafilcon A, Neofocon, Pasifocon, Telefocon, Silafocon, Fluorsilfocon, Paflufocon, Silafocon, Elastofilcon, Fluorofocon or Teflon AF materials, such as Teflon AF 1600 or Teflon AF 2400 which are copolymers of about 63 to 73 mol % of perfluoro-2,2-dimethyl-1,3-dioxol and about 37 to 27 mol % of tetrafluoroethylene, or of about 80 to 90 mol % of perfluoro-2,2-dimethyl-1,3-dioxol and about 20 to 10 mol % of tetrafluoroethylene.

Another group of preferred materials to be coated are amphiphilic segmented copolymers comprising at least one hydrophobic segment and at least one hydrophilic segment which are linked through a bond or a bridge member. Examples are silicone hydrogels, for example those disclosed in PCT applications WO 96/31792 and WO 97/49740.

The material to be coated may also be any blood-contacting material conventionally used for the manufacture of renal dialysis membranes, blood storage bags, pacemaker leads or vascular grafts. For example, the material to be modified on its surface may be a polyurethane, polydimethylsiloxane, polytetrafluoroethylene, polyvinylchloride, Dacron™ or a composite made therefrom.

Moreover, the material to be coated may also be an inorganic or metallic base material with or without suitable reactive groups, e.g. ceramic, quartz, or metals, such as silicon or gold, or other polymeric or non-polymeric substrates. E.g. for implantable biomedical applications, ceramics or carbohydrate containing materials such as polysaccharides are very useful. In addition, e.g. for biosensor purposes, dextran coated base materials are expected to reduce nonspecific binding effects if the structure of the coating is well controlled. Biosensors may require polysaccharides on gold, quartz, or other non-polymeric substrates.

The form of the material to be coated may vary within wide limits. Examples are particles, granules, capsules, fibres, and particularly moldings of all kinds, for example tubes, films, membranes or biomedical moldings, in particular ophthalmic moldings, such as contact lenses, intraocular lenses or artificial cornea. Further examples of moldings are materials useful for example as wound healing dressings, eye bandages, materials for the sustained release of an active compound such as a drug delivery patch, moldings that can be used in surgery, such as heart valves, vascular grafts, catheters, artificial organs, encapsulated biologic implants, e.g. pancreatic islets, materials for prostheses such as bone substitutes, or moldings for diagnostics, membranes or biomedical instruments or apparatus.

The compounds of formula (1) may be applied to the bulk material surface according to processes known per se. For example, the bulk material is immersed in a solution of a compound of formula (1), or a layer of a compound of formula (1) is first of all deposited on the modified bulk material surface, for example, by dipping, spraying, printing, spreading, pouring, rolling, spin coating or vacuum vapor deposition, dipping or especially spraying being preferred. Most preferably, a solution comprising one or more different compounds of the formula (1) is sprayed onto the bulk material surface which may be wet or preferably dry. According to a further preferred embodiment, the material to be coated is dipped in a solution of a compound of formula (1) in a solvent that is able to swell the material (swell-dipping).

Suitable solvents useful as solvents of the compounds of formula (1) are, for example, water, $C_1$–$C_4$-alkanols such as methanol, ethanol or iso-propanol, nitrites such as acetonitrile, tetrahydrofurane (THF), aqueous solutions comprising an alkanol, THF or the like, and also hydrocarbons, for example halogenated hydrocarbons such as methylene chloride or chloroform. The concentration of the compound of formula (1) in the spray solution depends on the specific compound used but is in general in the range of from 0.1 to 100 g/l, preferably 0.5 to 50 g/l, more preferably 0.5 to 25 g/l and in particular 1 to 10 g/l.

The fixation of the compounds of formula (1) on the bulk material surface then may be initiated, for example, by irradiation, particularly by irradiation with UV or visible light. Suitable light sources for the irradiation are known to the artisan and comprise for example mercury lamps, high pressure mercury lamps, xenon lamps, carbon arc lamps or sunlight. Sensitizers may be used to shift the irradiation wavelength. In addition, a suitable filter may be used to limit the irradiation to a specific wavelength range. Preferably, the bulk material surface to which have been previously applied the compound(s) of formula (1) is irradiated with light of a wavelength $\geq 300$ nm. The time period of irradiation is not critical but is usually in the range of up to 30 minutes, preferably from 10 seconds to 10 minutes, and more preferably from 15 seconds to 5 minutes, and particularly preferably from 20 seconds to 1 minute. It is advantageous to carry out the irradiation in an atmosphere of inert gas. After the polymerization, any non-covalently bonded polymers or non-reacted compound of formula (1) can be removed, for example by treatment, e.g. extraction, with suitable solvents, for example water, $C_1$–$C_4$-alkanols, water/$C_1$–$C_4$-alkanol mixtures or acetonitrile.

Depending on the desired properties and coating thickness the above outlined process cycle, (i) contacting, i.e. spraying or dipping, the surface with the compound(s) of formula (1) and (ii) fixing the compound(s) of formula (1) on the surface, i.e. by irradiation, may be carried out once or, preferably, several times. For example, 1 to 100, preferably 1 to 50 and in particular 5 to 25, different layers of one or more compounds of formula (1) are added and fixed on the bulk material surface. According to a further embodiment of the invention, the step (i) of contacting, i.e. spraying or dipping, the surface with the compound(s) of formula (1) is carried out several times, for example from 2 to 25 times and preferably from 2 to 10 times, and the fixation step (ii) is done only afterwards. If a process comprising several spraying or dipping steps is used, each spraying or dipping step may be carried out with the same polymer; alternatively different polymers may be used in each spraying or dipping step.

The thickness of the coating of the compound of formula (1) on the bulk material depends principally on the desired properties. It can be, for example, from 0.001 to 1000 $\mu$m, preferably from 0.005 to 100 $\mu$m, more preferably from 0.01 to 50 $\mu$m, even more preferably from 0.01 to 5 $\mu$m, especially preferably from 0.01 to 1 $\mu$m and particularly preferably from 0.01 to 0.5 $\mu$m.

The composite materials according to the invention and especially biomedical moldings comprising such a composite material have a variety of unexpected advantages over those of the prior art which make those moldings very suitable for practical purposes,e.g. as contact lens for extended wear or intraocular lens. For example, they do have a high surface wettability which can be demonstrated by their contact angles, their water retention and their water-film break up time or pre-lens or on-eye tear film break up time (TBUT).

The TBUT plays an particularly important role in the field of ophthalmic devices such as contact lenses. Thus the facile movement of an eyelid over a contact lens has proven important for the comfort of the wearer; this sliding motion is facilitated by the presence of a continuous layer of tear fluid on the contact lens, a layer which lubricates the tissue/lens interface. However, clinical tests have shown that currently available contact lenses partially dry out between blinks, thus increasing friction between eyelid and the lens. The increased friction results in soreness of the eyes and reduced movement of the contact lenses. Now it has become feasible to considerably increase the TBUT of commercial contact lenses such as, for example, Focus Dailies™, Focus New Vues® or Lotrafilcon A lenses, by applying a surface coating according to the invention. On the base curve of a contact lens, the pronounced lubricity of the coating facilitates the on-eye lens movement which is essential for extended wear of contact lenses. Moreover, the composite materials of the invention provide additional effects being essential for lenses for extended wear, such as an increased thickness of the pre-lens tear film which contributes substantially to low microbial adhesion and resistance to deposit formation. Due to the extremely soft and lubricious character of the surface of the composite materials, biomedical articles such as in particular contact lenses show a superior wearing comfort including improvements with respect to late day dryness and long term (overnight) wear. The surface of the composite materials of the present invention moreover interact in a reversible manner with occular mucus which contributes to the improved wearing comfort.

In addition, biomedical devices, e.g. ophthalmic devices such as contact lenses, comprising a composite material according to the present invention, have a very pronounced biocompatibility combined with good mechanical properties. For example, the devices are blood compatible and have a good tissue integration. In addition, there are generally no adverse eye effects observed, while the adsorption of proteins or lipids is low, also the salt deposit formation is lower than with conventional contact lenses. Generally, there is low fouling, low microbial adhesion and low bioerosion while good mechanical properties can be for example found in a low friction coefficient and low abrasion properties. Moreover, the dimensional stability of the composite materials of the invention is excellent. In addition, the attachment of a hydrophilic surface coating at a given bulk material according to the invention does not affect its visual transparency.

In summary, the ophthalmic devices comprising a composite material according to the present invention, such as contact lenses, artificial cornea or intraocular lenses, provide a combination of low spoilation with respect to cell debris, cosmetics, dust or dirt, solvent vapors or chemicals, with a high comfort for the patient wearing such opthalmic devices in view of the soft hydrogel surface which for example provides a very good on-eye movement of the ophthalmic device.

Biomedical devices such as renal dialysis membranes, blood storage bags, pacemaker leads or vascular grafts comprising a composite material according to the present invention resist fouling by proteins by virtue of the continuous layer of bound water, thus reducing the rate and extent of thrombosis. Blood-contacting devices fabricated according to the present invention are therefore haemocompatible and biocompatible.

In the examples, if not indicated otherwise, amounts are amounts by weight, temperatures are given in degrees Celsius. Tear break-up time values in general relate to the pre-lens tear film non-invasive break-up time (PLTF-NIBUT) that is determined following the procedure published by M. Guillon et al., Ophthal. Physiol. Opt. 9, 355–359 (1989) or M. Guillon et al., Optometry and Vision Science 74, 273–279 (1997). Average advancing and receding water contact angles of coated and non-coated lenses are determined with the dynamic Wilhelmy method using a Krüss K-12 instrument (Krüss GmbH, Hamburg, Germany). Wetting force on the solid is measured as the solid is immersed in or withdrawn from a liquid of known surface tension.

EXAMPLE 1
Synthesis of a Diazirine NHS Ester 7.06 g (36.81 mmol) N-ethyl-N'-(3-dimethylaminopropyl)carbodiimide hydrochloride are given into a 500 mL round bottom flask filled with 200 mL water at pH 12. After 15 minutes stirring at room temperature 50 mL dichlormethane are added. The extraction is repeated three times with 50 mL dichlormethane. The organic phases are combined, dried over $MgSO_4$, filtered and dried at high vacuum. The free base is given into a 250 mL round bottom flask and dissolved in 150 mL acetonitrile (28.4 ppm water). 17.19 g (~12 mmol Cl) Merrifield polymer is added. The suspension is heated to 100° C. under reflux for 16 hours. After cooling to room temperature the activated Merrifield polymer is washed 3 times with 50 mL acetonitrile, 2 times with 50 mL diethylether and dried at high vacuum. 300 mg (1.30 mmol) 4-(1-azi-2,2,2-trifluoroethyl)benzoic acid, 135 mg (1.17 mmol) N-hydroxysuccinimide, 6.3 g activated Merrifield polymer and 45 mL chloroform are given into a 100 mL brown round bottom flask and shaked at room temperature. DC control indicates complete conversion after 30 minutes. The mixture is filtered and washed with chloroform. The filtrate is dried at high vacuum. Complete reaction is determined by 1H-NMR spectroscopy.

EXAMPLE 2
Synthesis of a Monofunctional DMA Telomer

A carefully degassed solution of 293,3 g (3,0 mols) freshly distilled N,N-dimethyl-acrylamide, 37,2 g (0,327 mols) of cysteamine hydrochloride and 4,08 g of a,a-azodiisobutyramidine dihydrochloride in 600 ml of HPLC-grade water (pH adjusted to 3 using 10N HCl)) is slowly dropped into a 1000 ml reaction flask kept at 60° C. and purged with nitrogen. In order to keep the exothermic reaction under control the addition of the solution to the reaction flask occurs via a horizontal glass tube 60 cm in length and 1 cm wide which is heated to 60° C. The dropwise addition takes overall 90 minutes. Subsequently the reaction mixture is stirred under nitrogen at 60° C. for 4 hrs. The pH of the mixture is adjusted to 10.5 by addition of 1 molar sodium hydroxide solution and diluted to a total volume of 1200 mL. Salts and low molecular weight residues such as unreacted chain transfer agent are removed by reverse osmosis using a Millipore Proscale system equipped with a Millipore Helicon RO-4 Nanomax 50 membrane operating at a pressure of 15 bar. The product is isolated from the obtained retentate by freeze-drying.

EXAMPLE 2.1–2.3
Synthesis of Further Monofunctional Telomers

Following the procedure as outlined under Example 2 analogous N,N-dimethylacrylamide (DMA) and acrylamide (AAm) telomers of various molecular weights are prepared. The amounts of reagents used as well as the number average molecular weights obtained are listed in Table 1:

TABLE 1

| Example | DMA/AAm [mol] | Initiator [mMol] | Chain transfer agent [mMol] | $M_n$ |
|---------|---------------|------------------|------------------------------|-------|
| 2.1 | 2.0 DMA | 72.8 | 10.0 | 3800 |
| 2.2 | 2.0 DMA | 5.3 | 2.6 | 40100 |
| 2.3 | 1.0 AAm | 5.0 | 2.2 | 25000 |

EXAMPLE 3
Synthesis of DMA Telomer with Diazirine Head Group 2.0 g (0.53 mmol) amino terminated (0.264 mAeq/g) DMA telomer of Example 2.1, 173 mg (0.53 mmol) ) 4-(1-Azi-2,2,2-trifluoroethyl)benzoic NHS ester from Example 1 and 15 mL isopropanol are given into a 50 mL brown round bottom flask and shaked for 16 hours at room temperature. The mixture is then dried at high vacuum and dissolved in water. N-hydroxysuccinimide is removed by ultrafiltration using YC05 membrane. The compound is isolated by freeze drying; the degree of functionalization of 85% is terminated by $^1$H-NMR spectroscopy.

EXAMPLE 4
Synthesis of an AAm Telomer with Azido Head Group

A mixture of 2.0 g (0.08 mmol) amino terminated (0.04 mAeq amino/g) AAm telomer from Example 2.3 dissolved in 25 mL water and 14.5 mg (0.08 mmol) 4-azidophenyl-isothio-cyanate dissolved in 1 mL isopropanol are added in a 50 mL brown round bottom flask and stirred for 16 hours at room temperature. The mixture is dried at high vacuum, dissolved in water, and finally isolated by freeze drying. The degree of functionalization of >95% is determined by 1H-NMR spectroscopy.

EXAMPLE 5

Spray Coating of a DMA Telomer with Diazirine Head Group on a Contact Lens

An aqueous solution of 40 mg/mL of the DMA telomer with diazirine head group according to Example 3 is given into a funnel of an airbrush aero-pro 381™ (Hansa). The solution is sprayed on both sides of lotrafilcon A contact lenses (polysiloxane/perfluoroalkyl polyether copolymer) for 5 seconds using a nitrogen pressure of 1.15 bar. Afterwards the lenses are irradiated 30 seconds using UV LQ 400B lamp (Gröbel) with an intensity of 1.36 mW/cm$^2$ and a 305 nm cutoff filter. The whole process is repeated 10 times. The lenses are then extracted in water overnight and autoclaved. The wettability is monitored by dynamic contact angle measurements leading to advancing and receding contact angles of 66° and 28°.

EXAMPLE 6

Dip Coating on Contact Lenses using a DMA Telomer with Diazirine Head Group

Lotrafilcon A lenses are immersed into an aqueous solution of 100 mg/mL DMA with diazirine head group of Example 3 for 60 seconds. Afterwards the lenses are irradiated for 30 seconds using UV LQ 4006 lamp (Gröbel) with an intensity of 1.51 mW/cm$^2$ and a 305 nm cutoff filter. The whole process is repeated 9 times. The lenses are then extracted in water overnight and autoclaved. The wettability is monitored by dynamic contact angle measurements leading to advancing and receding contact angles of 67° and 21°.

EXAMPLE 7

Spray Coating on Contact Lenses using an AAm Telomer with Azido Head Group

An aqueous solution of 2 mg/mL acrylamide telomer with azido head group of Example 4 is given into a funnel of an airbrush aero-pro 381™ (Hansa). The solution is sprayed on both sides of lotrafilcon A lenses for 5 seconds using a nitrogen pressure of 1.2 bar. Afterwards the lenses are irradiated for 30 seconds using a UV LQ 400B lamp (Gröbel) with an intensity of 1.29 mW/cm$^2$ and a 305 nm cutoff filter. The whole process is repeated 10 times. The lenses are then extracted in water overnight and autoclaved. The wettability is monitored by dynamic contact angle measurements leading to advancing and receding contact angles of 80° and 20°.

What is claimed is:

1. A compound of formula

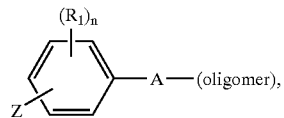
(1)

wherein $R_1$ is an electron-withdrawing substituent and n is an integer from 0 to 2, Z is a group which functions as a precursor for carbene or nitrene formation, A is a radical of formula

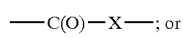
—C(O)—X—; or (2a)

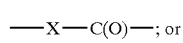
—X—C(O)—; or (2b)

-continued

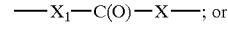
—X$_1$—C(O)—X—; or (2c)

—X$_1$—C(S)—X—; or (2d)

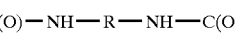
—A$_1$—C(O)—X—; or (2e)

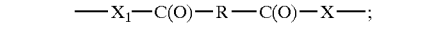
—X$_1$—C(O)—NH—R—NH—C(O)—X—; or (2f)

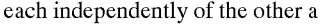
—X$_1$—C(O)—R—C(O)—X—; (2g)

X and X$_1$ are each independently of the other a group —O— or —NR$_2$—, wherein R$_2$ is hydrogen or C$_1$–C$_4$-alkyl;

A$_1$ is C$_2$–C$_{30}$-alkyl which may be Interrupted by —O—;

R is linear or branched C$_1$–C$_{18}$-alkylene or unsubstituted or C$_1$–C$_4$-alkyl- or C$_1$–C$_4$-alkoxy-substituted C$_6$–C$_{10}$-arylene, C$_7$–C$_{18}$-aralkylene, C$_6$–C$_{10}$-arylene-C$_1$–C$_2$-alkylene-C$_6$–C$_{10}$-arylene, C$_3$–C$_8$-cycloalkylene, C$_3$–C$_8$-cycloakylene-C$_1$–C$_6$-alkylene, C$_3$–C$_8$-cycloalkylene-C$_1$–C$_2$-alkylene-C$_3$–C$_8$-cycloalkylene or C$_1$–C$_6$-alkylene-C$_3$–C$_8$-cycloakylene-C$_1$–C$_8$-alkylene; and (oligomer) is (i) the radical of a telomer of formula

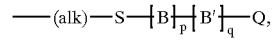
(3a)

wherein (alk) is C$_2$–C$_{12}$-alkylene,

Q is a monovalent group that is suitable to act as a polymerization chain-reaction terminator, p and q are each independently of another an integer from 0 to 750, wherein the total of (p+q) is an integer from 2 to 750, and B and B' are each independently of the other a 1,2-ethylene radical derivable from a copolymerizable vinyl monomer by replacing the vinylic double bond by a single bond, at least one of the radicals B and B' being substituted by a hydrophilic substituent; or (i-i) the radical of a telomer of formula

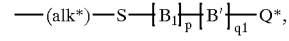
(3a-a)

wherein (alk*) Q*, p1 and q1 each independently have the meaning of (alk), Q, p and q, B$_1$ is a 1,2-ethylene radical derivable from a copolymerizable vinyl monomer by replacing the vinylic double bond by a single bond, which is substituted by a radical —T-(oligomer$_1$), wherein (oligomer$_1$) independently is a radical of formula (3a) above and T is is a direct bond or a radical of formula

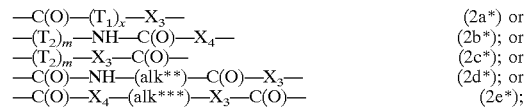

—C(O)—(T$_1$)$_x$—X$_3$— (2a*) or
—(T$_2$)$_m$—NH—C(O)—X$_4$— (2b*); or
—(T$_2$)$_m$—X$_3$—C(O)— (2c*); or
—C(O)—NH—(alk**)—C(O)—X$_3$— (2d*); or
—C(O)—X$_4$—(alk***)—X$_3$—C(O)— (2e*);

T$_1$ is —O—C$_2$–C$_{12}$-alkylene which is unsubstituted or substituted by hydroxy, or is —O—C$_2$–C$_{12}$-alkylene-NH—C(O)— or —O—C$_2$–C$_{12}$-alkylene-O—C(O)—NH—R$_{13}$—NH—C(O)—, wherein R$_{13}$ independently has the meaning of R above;

T$_2$ is C$_1$–C$_8$-alkylene; phenylene or benzylene;

X$_3$ and X$_4$ are each independently of the other a bivalent group —O— or —NR$_2$', wherein R$_2$' is hydrogen or C$_1$–C$_6$-alkyl;

(alk) is C$_1$–C$_6$-alkylene and (alk*) is C$_2$–C$_{12}$-alkylene, and m and x are each independently of the other the number 0 or 1; and $B_1'$ independently has the meaning of $B_1$ or B; or (ii) the radical of an oligomer of the formula $$-\!\!\left[CH_2-CH_2-N\right]_u\!\!-Q', \quad (3b)$$
$$\phantom{-\!\!\left[CH_2-CH_2-\right]}O\!=\!\!\underset{R_3}{C}$$

wherein $R_3$ is hydrogen or unsubstituted or hydroxy-substituted $C_1$–$C_{12}$-alkyl, u is an integer from 2 to 750 and 0' is a radical of a polymerization initiator, or (iii) the radical of formula $$\text{(aryl)}\!-\!CH_2\!\!-\!\!\left[N-CH_2-CH_2\right]_u\!\!-X_2H, \quad (3b')$$
$$\phantom{-\!\!\left[CH_2\right]}\underset{R_3}{|}$$
$$\phantom{-\!\!\left[CH_2\right]}C\!=\!O$$

wherein $X_2$ independently has the meaning of X above, and $R_3$ and u are as defined above, or (iv) the radical of an oligomer of formula $$-\!\!\left[\underset{\substack{|\\ \underset{R_4\ R_4'}{N^+}\ An^-}}{CH}\!\!\underset{CH_2}{\overset{CH_2}{<}}\!CH\!-\!CH_2\right]_v\!\!-Q'', \quad (3c)$$

wherein $R_4$ and $R_4'$ are each independently $C_1$–$C_4$-alkyl, $An^{31}$ is an anion, v is an integer from 2 to 750, and Q" is a monovalent group that is suitable to act as a polymerization chain-reaction terminator;

subject to the proviso that A is not a radical of formula (2b) if (oligomer) is a radical of formula (3b) or (3c).

2. A compound according to claim 1, wherein Z is a group of formula $$\begin{array}{c}N\\\diagup\diagdown\\\hspace{-1em}-\hspace{-0.5em}\big|\hspace{1em}N\\R_5\end{array} \quad \text{or} \quad (4a)$$

$$-N_3, \quad (4b)$$

wherein $R_2$ is fluorinated $C_1$–$C_6$-alkyl.

3. A compound according to claim 1, wherein Z is a group $$\begin{array}{c}N\\\diagup\diagdown\\\hspace{-1em}-\hspace{-0.5em}\big|\hspace{1em}N,\\CF_3\end{array}$$

n is 0, and A is a radical of formula (2a).

4. A compound according to claim 1, wherein Z is a group $-N_3$, n is 0 or 1, and A is a radical of formula (2b), (2d) or (2e).

5. A compound according to claim 1, wherein (oligomer) is a telomer radical of formula (3a).

6. A compound according to claim 5, wherein the hydrophilic substituent of the radicals B and B' is selected from the group consisting of a radical —COOY, a radical —CO—$NY_1Y_2$, and a heterocyclic radical, wherein Y is $C_{1-C2}$-alkyl, substituted $C_2$–$C_3$-alkyl, or is a radical —$C_2$–$C_4$-alkylene-NH—C(O)—O—G, wherein the substituted $C_2$–$C_3$-alkyl is substituted by hydroxy, amino or N,N-di-$C_1$–$C_2$-alkylamino, wherein —O—G is the radical of trehalose or a cyclo-dextrin fragment with a maximum of 8 sugar units, wherein $Y_1$ and $Y_2$ are each independently of the other hydrogen, $C_1$–$C_2$-alkyl or $C_1$–$C_4$-alkyl which is substituted by hydroxy, or $Y_1$ and $Y_2$ together with the adjacent N-atom form a N—$C_1$–$C_2$-alkylpiperazino or morpholino ring; and wherein the heterocyclic radical is selected from the group consisting of N-pyrrolidonyl, 2-pyridinyl, 4-pyridinyl, 2-methylpyridin-5-yl, 2-, 3- oder 4-hydroxypyridinyl, N-ϵ-caprolactamyl, N-imidazolyl, 2-methylimidazol-1-yl, N-morpholinyl and 4-N-methylpiperazin-1-yl.

7. A compound according to claim 1, wherein (oligomer) is a a radical of formula $$-\!(alk)\!-\!S\!-\!\!\left[CH_2\!-\!\underset{\underset{R_{10}}{|}}{\overset{\overset{R_9}{|}}{C}}\right]_p\!\!\left[CH_2\!-\!\underset{\underset{R_{10}'}{|}}{\overset{\overset{R_9'}{|}}{C}}\right]_q\!\!-Q, \quad (3a')$$

wherein (alk) is $C_2$–$C_4$-alkylene, $R_9$ and $R_9'$ are each independently of the other hydrogen or methyl, Q is a monovalent group that is suitable to act as a polymerization chain-reaction terminator, $R_{10}$ and $R_{10}'$ are each independently of the other —COO—$C_1$–$C_2$-alkyl, —COO—$(CH_2)_{2-4}$—OH, —$CONH_2$, —$CON(CH_3)_2$, —CONH—$(CH_2)_2$—OH, $$\begin{array}{c}O\\\|\\-C-N\diagdown\underset{CH_2CH_2-OH,}{C_1-C_2-alkyl}\end{array} \quad \begin{array}{c}O\\\|\\-C-N\diagdown\diagup O,\end{array} \quad -N\diagdown\diagup\underset{O}{}$$

or —$COO(CH_2)_{2-4}$—NHC(O)—O—G wherein —O—G is the radical of trehalose or a cyclodextrin fragment with a maximum of 8 sugar units, and p and q are each independently of another an integer from 0 to 750, wherein the total of (p+q) is an integer from 2 to 750.

8. A compound according to claim 7, wherein p is an integer from 10 to 750, q is 0, and $R_{10}$ is —COO—$(CH_2)_{2-4}$—OH, —$CONH_2$, —$CON(CH_3)_2$, $$\begin{array}{c}O\\\|\\-C-N\diagdown\diagup O,\end{array} \quad \text{or} \quad -N\diagdown\diagup\underset{O}{}.$$

* * * * *